United States Patent [19]

Barton et al.

[11] 4,354,034

[45] * Oct. 12, 1982

[54] DIHALOPHENOXYPROPIONIC ACIDS AND THEIR DERIVATIVES, AND THEIR USE AS COTTON DESICCANTS

[75] Inventors: John E. Barton, Wokingham; David J. Collins, Crowthorne; Donald W. Headford, Reading, all of England

[73] Assignee: Imperial Chemical Industries Limited, London, England

[*] Notice: The portion of the term of this patent subsequent to Mar. 24, 1998, has been disclaimed.

[21] Appl. No.: 48,771

[22] Filed: Jun. 15, 1979

[30] Foreign Application Priority Data

Jun. 30, 1978 [GB] United Kingdom ............... 28420/78

[51] Int. Cl.$^3$ ............................................. C07C 69/76
[52] U.S. Cl. ......................................... 560/62; 71/70; 71/108; 560/63; 562/472
[58] Field of Search .................... 560/62, 63; 562/472; 71/70, 108

[56] References Cited

U.S. PATENT DOCUMENTS 3,362,997 1/1968 Bolhofer ............................... 560/62
4,051,184 9/1977 Arneklev et al. .

FOREIGN PATENT DOCUMENTS 477392 10/1969 Switzerland ......................... 560/63
720838 12/1954 United Kingdom .................. 560/63

OTHER PUBLICATIONS

Chem. Abst. 108899n, vol. 75, 1971.

Primary Examiner—Paul J. Killos
Attorney, Agent, or Firm—Cushman, Darby & Cushman

[57] ABSTRACT

This invention relates to dihalophenoxypropionic acids and their derivatives useful for desiccating cotton plants, to a process for preparing these compounds, to cotton desiccating compositions containing them and to a method of desiccating cotton using them.

1 Claim, No Drawings

DIHALOPHENOXYPROPIONIC ACIDS AND THEIR DERIVATIVES, AND THEIR USE AS COTTON DESICCANTS

In the mechanical harvesting of cotton crops, the presence of green leaves and stems on the cotton plants is disadvantageous, since the leaves and stems tend to be crushed during the harvesting operation, and to leave green stains on the cotton. Accordingly it is general practice to spray the crop, at a convenient interval before harvesting, with a chemical desiccant in order to dry up the green leaves and stems.

Our British patent application No. 9878/77 (U.S. Ser. No. 881,065, filed Feb. 24, 1978) relates to the use as desiccants for cotton of compounds of general formula (I):

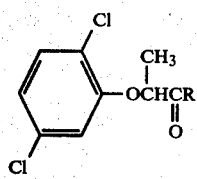

wherein R is hydroxy, a group of general formula —OM wherein M is a cation, or one of a variety of optionally substituted alkoxy, alkenyloxy, phenoxy and amino groups. We have now discovered a further class of compounds having cotton desiccating activity.

Accordingly, the present invention provides a compound of general formula (II):

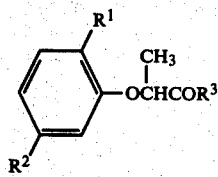

wherein each of $R^1$ and $R^2$, which may be the same or different, is halogen or halo ($C_{1-6}$ alkyl) (e.g. trifluoromethyl); and $R^3$ is hydroxy; a group of general formula —OM wherein M is a cation; phenoxy optionally substituted with at least one substituent selected from the class consisting of halogen and $C_{1-4}$ alkyl; cycloalkoxy; alkoxy optionally substituted with at least one substituent selected from the class consisting of chlorine, hydroxy, alkoxy, dialkylamino, optionally chloro-, phenoxy- or methyl- substituted phenyl and a group of general formula (III):

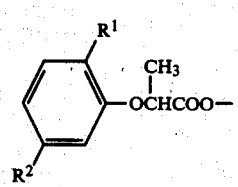

wherein $R^1$ and $R^2$ are as defined above; alkenyloxy; alkylthio optionally substituted with optionally chloro- or methyl-substituted phenyl; alkenylthio; or a group of general formula —$NR^4R^5$ wherein $R^4$ is hydrogen, alkoxy, alkyl, alkenyl, phenyl or mono- or di-alkylamino, and $R^5$ is hydrogen, alkyl, alkenyl or alkanesulphonyl, or $R^4$ and $R^5$ form, together with the nitrogen to which they are attached, a pyrrolidine or piperidine ring; subject to the proviso that $R^1$ and $R^2$ are both chlorine only when $R^3$ is a group of formula —$NR^4R^5$ wherein $R^4$ is hydrogen and $R^5$ is alkanesulphonyl.

In this specification, the terms "halogen" and "halo" refer only to fluorine, chlorine, bromine and iodine.

When M is a cation it may be for example an alkali metal or an alkaline earth metal cation, for example a sodium, potassium, calcium or magnesium cation. M can also be an ammonium cation or a mono-, di-, tri- or tetra- substituted ammonium cation in which the substituents may be, for example, $C_{1-6}$ aliphatic groups. e.g. $C_{1-6}$ alkyl groups.

When $R^3$ is alkoxy, it may be for example $C_{1-20}$ alkoxy, for example $C_{1-12}$ alkoxy e.g. methoxy, ethoxy, propoxy, isopropoxy, butoxy, pentyloxy, hexyloxy, octyloxy and dodecyloxy. When $R^3$ is substituted alkoxy, it may be benzyloxy optionally substituted by at least one chlorine or methyl, for example 2-chlorobenzyloxy, 3-chlorobenzyloxy, 4-chlorobenzyloxy, 2,4-dichlorobenzyloxy, 4-methylbenzyloxy or 4-phenoxybenzyloxy. The substituted alkoxy groups can also be alkoxy substituted by at least one hydroxy, alkoxy (for example $C_{1-4}$ alkoxy), chlorine, dialkylamino or a group of general formula (III) as defined above, e.g. 2-hydroxyethoxy, 2-chloroethoxy, 2-diethylaminoethoxy, 2-ethoxyethoxy, 2-butoxyethoxy or 2[α-(2,5-dibromophenoxy)propionyloxy]ethoxy. When $R^3$ is cycloalkoxy, it is suitably $C_{3-6}$ cycloalkoxy e.g. cyclohexyloxy.

When $R^3$ is alkenyloxy, it may be $C_{3-20}$ alkenyloxy e.g. $C_{3-12}$ alkenyloxy; examples are allyloxy and octadecenyloxy.

Examples of alkylthio groups are $C_{1-12}$ alkylthio, e.g. methylthio and ethylthio. Examples of substituted alkylthio groups are benzylthio optionally ring-substituted with at least one methyl or chlorine, for example 2-chlorobenzylthio, 3-chlorobenzylthio, 4-chlorobenzylthio, and 4-methylbenzylthio.

Examples of alkenylthio radicals are $C_{3-12}$ alkenylthio, e.g. allylthio.

When $R^4$ is alkoxy, it may be for example $C_{1-12}$ alkoxy, e.g. methoxy. When $R^4$ is alkyl, it may be for example methyl, ethyl, propyl or butyl. When $R^4$ is alkenyl, it may be for example allyl or but-2-enyl. When $R^4$ is mono- or di- alkylamino, the alkyl can be $C_{1-4}$ alkyl. When $R^5$ is alkyl, it may for example be $C_{1-4}$ alkyl. When $R^5$ is alkenyl, it may be allyl or but-2-enyl. When $R^5$ is alkanesulphonyl, it may be for example $C_{1-4}$ alkanesulphonyl e.g. methanesulphonyl.

Examples of the compounds of general formula (II) are listed in Table I:

TABLE I

| Compound No | $R^1$ | $R^2$ | $R^3$ | Melting (or Boiling) Point (°C.) |
|---|---|---|---|---|
| 1 | Br | Br | EtO— | (118–123°/0.2 Torr) |
| 2 | Br | Br | $H_2N$— | 142° |
| 3 | Br | Br | HO— | 143° |
| 4 | Br | Br | $C_6H_5CH_2O$— | 52° |
| 5 | Br | Cl | EtO— | (106–107°/0.4 Torr) |
| 6 | Cl | Br | EtO— | (116–117°/0.4 Torr) |
| 7 | Br | Cl | HO— | 143° |
| 8 | Cl | Br | HO— | 135° |
| 9 | Cl | $CF_3$ | $Me_2N$— | 62–63° |
| 10 | Br | Br | $Me_2N$— | 84° |
| 11 | Br | Cl | $Me_2N$— | 76° |
| 12 | Cl | Br | $Me_2N$— | 88° |
| 13 | Cl | I | $Me_2N$— | 105° |
| 14 | Cl | Br | $C_6H_5CH_2O$— | 48–50° |

TABLE I-continued

| Compound No | R¹ | R² | R³ | Melting (or Boiling) Point (°C.) |
|---|---|---|---|---|
| 15 | Br | I | EtO— | 40° |
| 16 | Br | I | C₆H₅CH₂O— | |
| 17 | Br | I | Me₂N— | 109° |
| 18 | Cl | I | EtO— | (150°/0.1 Torr) |
| 19 | Cl | CF₃ | EtO— | (77–78°/0.6 Torr) |
| 20 | Br | Cl | C₆H₅CH₂O— | 49–53° |
| 21 | Br | Br | MeS(O)₂NH— | 144–145° |
| 22 | Br | Br | p-Cl—C₆H₄CH₂O— | 48–52° |
| 23 | Br | Br | p-C₆H₅O—C₆H₄CH₂O— | oil |

The compounds of general formula (II) may, if desired, be applied in admixture with other herbicides to desiccate cotton. Examples of these other herbicides are salts of the bipyridylium herbicides paraquat and diquat. Paraquat and diquat are the accepted common names for the 1,1'-dimethyl-4,4'-bipyridylium cation and the 1,1'-ethylene-2,2'-bipyridylium cation, respectively.

The particular salt of paraquat or diquat used is not critical. Conveniently the salt is one which is readily soluble in water. Examples of suitable paraquat salts are the chloride, bromide, iodide, methylsulphate, sulphate, methylphosphate, and phosphate while examples of suitable diquat salts are the chloride, bromide, iodide, methylsulphate, sulphate, phosphate and p-toluenesulphonate. Since the characteristic herbicidal activity of paraquat and diquat salts resides in the paraquat or diquat cation only, it is customary to quote concentrations of active ingredient and rates of application in terms of the amount of paraquat cation or diquat cation used, thus avoiding the inconvenience of having to quote different application rates for different salts of paraquat or diquat. Application rates and concentrations quoted in this Specification therefore relate to the amount of paraquat or diquat cation unless otherwise stated.

The rate at which the compounds of general formula (II) are applied to desiccate cotton depends upon a variety of factors, for example the identity of the particular compound chosen for use, but in general the rate is 0.06 to 1.0, e.g. 0.1 to 0.5, kilograms per hectare. When applied in admixture with paraquat or diquat, the amount of the compound can be correspondingly reduced; usually up to half or more of the weight of the compound can be replaced by the same weight of paraquat or diquat. Thus, instead of using 0.5 kilograms per hectare of the compound, a mixture of the compound and paraquat could be applied, each at a rate of 0.25 kilograms per hectare. An advantage of using the mixture is that the desiccation process is more rapid than when the compound is used alone.

The compounds are preferably applied in the form of compositions, in which the active ingredient is mixed with a carrier comprising a solid or liquid diluent. Preferably, a surface-active agent is also present. Conveniently, the compound is applied in the form of a solution or dispersion in water, together with a surface-active agent. When applied together with paraquat or diquat, the spray composition may comprise a solution of the compound in a water-immiscible organic solvent which has been emulsified with an aqueous solution of paraquat or diquat, the mixture containing a surface-active agent to assist in its emulsification. Examples of water-immiscible organic solvents include hydrocarbon solvents, for example alkyl-substituted benzenes, and chlorinated hydrocarbons, for example ethylene dichloride.

The compounds are preferably applied in the form of compositions in which the active ingredient is mixed with a carrier comprising a solid or liquid diluent. Preferably a surface-active agent is also present. Conveniently, the compounds are applied in the form of a solution or dispersion in water, together with a surface-active agent.

Surface active agents may be of the cationic, anionic or non-ionic type. Suitable cationic agents are quaternary ammonium compounds, for example cetyl-trimethyl ammonium bromide. Suitable anionic agents are soaps, salts of aliphatic monoesters of sulphuric acid, for example sodium lauryl sulphate, and salts of sulphonated aromatic compounds, for example dodecylbenzenesulphonate, sodium, calcium and ammonium ligno-sulphonate, butylnaphthalene sulphonate, and a mixture of the sodium salts of diisopropyl and triisopropyl-naphthalenesulphonic acid. Suitable non-ionic agents are the condensation products of ethylene oxide with fatty alcohols such as oleyl alcohol and cetyl alcohol, or with alkylphenols such as octylphenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins. When preparing compositions containing paraquat or diquat, anionic surface-active agents are generally to be avoided since they may interact unfavourably with these cationic herbicides.

For convenience in transport, storage and sale, there may be prepared concentrated compositions containing a high proportion of active ingredient, for example 10 to 85%, and 25 to 60%, by weight of active ingredient. These concentrates are diluted with water before use.

The compounds of general formula (II) may be made by conventional methods known in the art. The invention provides a process for preparing a compound of general formula (II), the process comprising (1) when a compound of general formula (II) wherein R³ is a group of general formula —OM as defined above, optionally substituted phenoxy, cycloalkoxy, optionally substituted alkoxy, alkenylthio, alkenyloxy, or optionally substituted alkylthio is required, reacting a compound of general formula (IV)

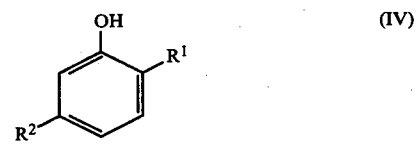

(IV)

wherein R¹ and R² are as defined above, with a compound of general formula (V)

(V)

R³ is as defined above and X is halogen (e.g. chlorine or bromine); or (2) when a compound of general formula (II) wherein R³ is hydroxy is required, hydrolysing a compound of general formula (II) wherein R³ is as defined above other than hydroxy; or (3) when a compound of general formula (III) wherein $R^3$ is a group of general formula $-NR^4R^5$ as defined above is required, reacting a compound of general formula (VI)

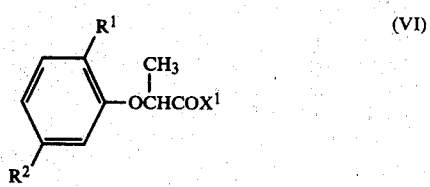

wherein $R^1$ and $R^2$ are as defined above, and $X^1$ is halogen (e.g. chlorine or bromine), with a compound of general formula (VII)

wherein $R^4$ and $R^5$ are as defined above;

and when $R^3$ in the compound of general formula (II) obtained in (1), (2) or (3) is not the desired group, converting it in known manner to give the compound of general formula (II) wherein $R^3$ is the desired group.

Process (1) is suitably performed in the presence of a base, e.g. an alkali metal hydroxide or carbonate, for example potassium carbonate, and should be present in an amount which is substantially equimolar with the other reactants. Preferably the reaction is carried out in an inert solvent, e.g. methyl ethyl ketone. The reaction may be accelerated by heating.

The acids from process (2) may be used as intermediates to obtain other compounds of general formula (II). Thus, by reaction with the appropriate alcohol, they may be converted according to standard methods to the compounds of general formula (II) wherein $R^3$ is, for example, alkoxy or alkenyloxy.

The invention also provides cotton desiccating compositions containing a compound of general formula (II) and a carrier or diluent.

It also provides a method of desiccating growing cotton plants, which method comprises applying to the foliage of the plants a compound of general formula (II).

The invention is illustrated by the following Examples, in which all temperatures are in degrees Centigrade and all parts are by weight unless otherwise specified.

EXAMPLE 1

This Example illustrates the use of the compounds of general formula (II) for desiccating cotton.

Each compound was formulated for test by dissolving it in cyclohexanone containing 33.3 grams per liter of Synperonic NPE 1800 (a surface-active agent comprising a condensate of one molar proportion of nonylphenol with 33 molar proportions of propylene oxide and 13 to 15 molar proportions of ethylene oxide) and 16.7 grams per liter of Tween 85 (a surface-active agent comprising a condensate of one molar proportion of sorbitan tri-oleate with twenty molar proportions of ethylene oxide). The cyclohexanone solution so prepared contained 1 gram of the compound per liter, calculated as the free acid. The solution was then diluted to 10 times its volume with cyclohexanone to give a stock solution. Samples of this were then dispersed in water to prepare emulsions for spraying. The spray emulsions so prepared were sprayed on to young rape, soya, and cotton plants grown in plastic pots of soil in the glass house. The rape plants were at the two true leaf stage, the soya plants had from one to two trifoliate leaves, and the cotton plants had two to three true leaves. The spray volume was equivalent to 200 liters per hectare. Twenty days after spraying, the extent of desiccation of the plants was assessed on a scale of 0 to 10. Each result given in Table II is the average value for three plants, rounded off to the nearest whole number.

TABLE II

| Compound No. | Rate of Application, kg/ha | Test Plants | | |
|---|---|---|---|---|
| | | Rape | Soya | Cotton |
| 1 | 0.05 | 1 | 0 | 3 |
| | 0.1 | 4 | 0 | 4 |
| | 0.5 | 8 | 4 | 9 |
| | 1.0 | 9 | 5 | 9 |
| | 2.0 | 10 | 8 | 9 |
| 4 | 0.05 | 2 | 0 | 9 |
| | 0.1 | 3 | 0 | 8 |
| | 0.5 | 7 | 5 | 10 |
| | 1.0 | 9 | 6 | 10 |
| | 2.0 | 10 | 8 | 10 |
| 5 | 0.05 | 1 | 0 | 1 |
| | 0.1 | 2 | 0 | 3 |
| | 0.5 | 8 | 5 | 8 |
| | 1.0 | 9 | 6 | 9 |
| | 2.0 | 9 | 8 | 10 |
| 6 | 0.05 | 2 | 0 | 3 |
| | 0.1 | 2 | 1 | 4 |
| | 0.5 | 9 | 6 | 8 |
| | 1.0 | 10 | 8 | 9 |
| | 2.0 | 10 | 10 | 9 |
| 9 | 0.1 | 0 | 0 | 1 |
| | 0.5 | 0 | 0 | 0 |
| | 1.0 | 0 | 0 | 3 |
| | 2.0 | 0 | 2 | 4 |
| | 5.0 | 0 | 4 | 8 |
| 10 | 0.1 | 0 | 0 | 0 |
| | 0.5 | 0 | 0 | 1 |
| | 1.0 | 0 | 0 | 6 |
| | 2.0 | 0 | 2 | 6 |
| | 5.0 | 0 | 5 | 9 |
| 11 | 0.1 | 0 | 0 | 2 |
| | 0.5 | 0 | 0 | 1 |
| | 1.0 | 0 | 1 | 7 |
| | 2.0 | 0 | 1 | 9 |
| | 5.0 | 1 | 6 | 10 |
| 12 | 0.1 | 0 | 0 | 0 |
| | 0.5 | 0 | 0 | 2 |
| | 1.0 | 0 | 0 | 1 |
| | 2.0 | 0 | 2 | 9 |
| | 5.0 | 2 | 5 | 9 |
| 13 | 0.1 | 0 | 0 | 0 |
| | 0.5 | 0 | 1 | 0 |
| | 1.0 | 0 | 1 | 3 |
| | 2.0 | 0 | 2 | 7 |
| | 5.0 | 1 | 5 | 8 |
| 14 | 0.05 | 2 | 0 | 6 |
| | 0.1 | 2 | 1 | 7 |
| | 0.5 | 10 | 7 | 10 |
| | 1.0 | 10 | 10 | 10 |
| | 2.0 | 10 | 10 | 10 |
| 15 | 0.05 | 2 | 0 | 1 |
| | 0.1 | 3 | 0 | 2 |
| | 0.5 | 6 | 2 | 8 |
| | 1.0 | 8 | 4 | 9 |
| | 2.0 | 9 | 7 | 9 |
| 16 | 0.05 | 2 | 0 | 7 |
| | 0.1 | 3 | 0 | 8 |
| | 0.5 | 6 | 2 | 9 |
| | 1.0 | 8 | 5 | 10 |
| | 2.0 | 9 | 6 | 10 |
| 17 | 0.1 | 0 | 0 | 0 |
| | 0.5 | 0 | 0 | 1 |
| | 1.0 | 0 | 0 | 1 |
| | 2.0 | 0 | 1 | 6 |
| | 5.0 | 0 | 4 | 8 |
| 18 | 0.05 | 2 | 0 | 3 |
| | 0.1 | 4 | 0 | 3 |
| | 0.5 | 9 | 5 | 8 |

TABLE II-continued

| Compound No. | Rate of Application, kg/ha | Rape | Soya | Cotton |
|---|---|---|---|---|
|  | 1.0 | 10 | 8 | 8 |
|  | 2.0 | 10 | 8 | 9 |
| 19 | 0.05 | 1 | 1 | 1 |
|  | 0.1 | 1 | 1 | 1 |
|  | 0.5 | 6 | 3 | 2 |
|  | 1.0 | 10 | 7 | 6 |
|  | 2.0 | 10 | 10 | 9 |
| 20 | 0.05 | 0 | 0 | 6 |
|  | 0.1 | 2 | 0 | 9 |
|  | 0.5 | 5 | 3 | 10 |
|  | 1.0 | 9 | 9 | 10 |
|  | 2.0 | 10 | 9 | 10 |

EXAMPLE 2

Benzyl (2,5-dibromophenoxy)propionate (Compound No. 4)

Stage 1

2-Bromopropionyl chloride (213.4 g) was added dropwise to benzyl alcohol (145.8 g) with stirring under a stream of nitrogen, keeping the temperature of the reaction mixture below 30° C. by cooling with cold water. When all the acid chloride has been added, the mixture was stirred for another two hours at ambient temperature. The reaction mixture was then diluted with diethyl ether (200 ml) and washed with water until free of acid. The ethereal solution was dried and evaporated and the residue distilled to give benzyl 2-bromopropionate, b.p. 82°–85°/0.5 Torr.

Stage 2

2,5-Dibromophenol (53 g) and benzyl 2-bromopropionate (48.6 g) in methyl iso-butyl ketone (250 ml) containing suspended potassium carbonate (13.8 g) was heated under reflux with stirring overnight. The mixture was cooled to 40°, 5% sodium hydroxide solution (100 ml) was added, and the mixture was stirred to dissolve the solid potassium bromide. The aqueous phase was separated with fresh methyl iso-butyl ketone (50 ml). The combined extracts were washed with water (50 ml), dried, and evaporated under reduced pressure. The residue was distilled and the benzyl (2,5-dibromophenoxy)propionate collected at 180°–185°/0.5 Torr. On cooling, the distillate solidified and had a melting point of 52° C. Compounds 1, 5, 6, 14 to 16, 18 to 20, 22 and 23 were made by a similar procedure.

EXAMPLE 3

2-(2-Bromo-5-chlorophenoxy)-N,N-dimethylpropionamide (Compound no. 11)

2-Bromo-5-chlorophenol (8 g), 2-bromo-N,N-dimethylpropionamide (6.66 g) and anhydrous potassium carbonate (2.6 g) in methyl iso-butyl ketone (100 ml) were refluxed with stirring overnight. The mixture was cooled to 50° and washed with 5% sodium hydroxide (2×20 ml) and then water (2×50 ml). The organic solution was dried and evaporated under reduced pressure to yield a pale red oil, which solidified on cooling. Recrystallisation from 50% aqueous ethanol gave the title compound, m.p. 76°–77°. Compounds 2, 9, 10 to 13, 17 and 21 were made by a similar procedure.

We claim:

1. A method of desiccating growing cotton plants, the method consisting essentially of the step of applying to the foliage of the plants, a cotton desiccating amount of a compound of general formula (II)

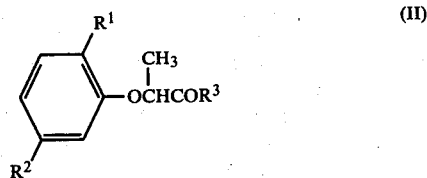

(II)

wherein one of $R^1$ and $R^2$ is bromine and the other is chlorine, bromine, iodine or trifluoromethyl; and $R^3$ is hydroxy; a group of general formula —OM wherein M is a cation; phenoxy optionally substituted with at least one substituent selected from the class consisting of halogen and $C_{1-4}$ alkyl; $C_{3-6}$ cycloalkoxy; $C_{1-12}$ alkoxy optionally substituted with at least one substituent selected from the class consisting of chlorine, hydroxy, $C_{1-4}$ alkoxy, di-($C_{1-4}$alkyl)-amino, optionally chloro-, phenoxy- or methyl-substituted phenyl and a group of general formula (III):

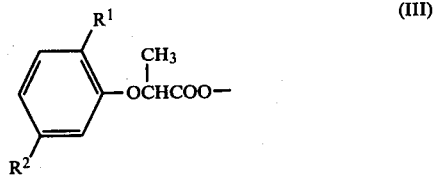

(III)

wherein $R^1$ and $R^2$ are as defined above or $C_{3-12}$ alkenyloxy.

* * * * *